(12) United States Patent
Nachum

(10) Patent No.: US 7,991,476 B2
(45) Date of Patent: Aug. 2, 2011

(54) METHOD AND DEVICE FOR ENHANCED BLOOD FLOW

(75) Inventor: Zvi Nachum, Tiberias (IL)

(73) Assignee: Empire Bio-Medical Devices, Inc., Brooklyn, NY (US)

( * ) Notice: Subject to any disclaimer, the term of this patent is extended or adjusted under 35 U.S.C. 154(b) by 1028 days.

(21) Appl. No.: 11/438,070

(22) Filed: May 22, 2006

(65) Prior Publication Data

US 2007/0270917 A1    Nov. 22, 2007

(51) Int. Cl.
    *A61N 1/00*    (2006.01)
(52) U.S. Cl. .......................................... 607/48
(58) Field of Classification Search .............. 607/48–49, 607/44
    See application file for complete search history.

(56) References Cited

U.S. PATENT DOCUMENTS

| 5,358,513 A * | 10/1994 | Powell et al. ............ 607/48 |
| 5,556,422 A | 9/1996 | Powell, III et al. |
| 5,674,262 A | 10/1997 | Tumey |
| 6,944,503 B2 | 9/2005 | Crowe et al. |

OTHER PUBLICATIONS

U.S. Appl. No. 10/451,334, filed Mar. 2004, Nachum, Zvi.

* cited by examiner

*Primary Examiner* — Mark W Bockelman

(57) ABSTRACT

A non-invasive method and device for promoting a localized change in a flow of blood through a limb segment by a series of electrically stimulated contractions of muscle tissue, the method including: (a) providing a device including: (i) at least a first electrode, a second electrode, and a third electrode, each of the electrodes for operatively contacting the limb segment of the body; (ii) a signal generator, operatively connected to each electrode, for producing a series of electrical impulses to the limb segment via the electrodes, and (iii) a control unit, associated with the signal generator, for controlling the signal generator so as to produce the series of electrical stimulation impulses; (b) positioning the plurality of electrodes on the limb segment; (c) applying electrical impulses to induce a substantially radial contraction of a first portion of the muscular tissue in the limb segment; (d) applying electrical impulses to induce a substantially longitudinal contraction of a second portion of the muscular tissue in the limb segment, such that the muscular tissue acts upon the blood vessel to produce the localized change in the flow of blood.

25 Claims, 10 Drawing Sheets
(3 of 10 Drawing Sheet(s) Filed in Color)

METHOD AND DEVICE FOR ENHANCED BLOOD FLOW

FIELD AND BACKGROUND OF THE INVENTION

The present invention relates to a method and device for promoting a localized change in the flow of blood through a blood vessel, and more particularly, to a non-invasive method and device for promoting a localized change in the flow of blood by electrically-induced contractual movement of muscular tissue.

Current treatments for improving blood circulation and alleviating neural and muscle pain include manual, electrical, and mechanical methods. Manual treatment as practiced in physiotherapy requires massaging to be administered by qualified personnel. The efficacy of this personnel-intensive art varies with the experience and technique of the individual massage therapist, and therefore cannot be prescribed in an adequately standardized form. More importantly, the improvement in blood circulation is also of an extremely limited magnitude.

Electrical Muscle Stimulation (EMS) has seen widespread use in many applications. The Food and Drug Administration (Section 355.200 Electrical Muscle Stimulators, CPG 7124.26) maintains that EMS devices are recognized in the health care community as being effective for muscle reeducation, relief of muscle spasm, increasing range of motion, disuse atrophy therapy, increased local blood circulation, and immediate post-surgical stimulation of calf muscles to prevent venous thrombosis. It must be emphasized, however, that the stimulation provided by EMS is very similar to the stimulation achieved by therapeutic massage. Any increase in blood circulation is so modest that it is often undetectable using conventional flow-measuring equipment. EMS is a random excitation of a local tissue area. Hence, EMS methods, like therapeutic massage, hot-water treatments, etc. are incapable of providing a major increase in the localized flow of blood. Moreover, because the excitation is random, EMS methods are fundamentally incapable of providing a decrease in the localized flow of blood.

Also known is a sequential pneumatic device for the reduction of an edema. The device consists of several overlapping compartments contained in a sleeve assembly. The compartments are inflated in a sequential fashion, from a distal end disposed adjacent to the edema, to a proximal end, such that the edema is pressed in the proximal direction. Each compartment is filled with air by a pump. The cycle starts with the filling of the distal compartment, and subsequently the remaining compartments are filled until all compartments are full. After a deflation period, the cycle is repeated.

This and other treatments employ electromechanical installations in which electric motors and reciprocating mechanisms create uncomfortable noise and vibration. These treatments are of further disadvantage in that they require various device elements to be contacted with the skin. These elements generally cause discomfort to the patient, and require changing and cleaning after each use in order to ensure good sanitary conditions.

U.S. Pat. No. 5,674,262 to Tumey teaches a device and method for stimulating blood flow velocity in a leg, in an effective and relatively painless manner, so as to prevent deep vein thrombosis. The device includes a mechanical compressing apparatus for compressing a foot so as to drive a substantial amount of blood from veins of the foot into blood vessels of the leg, and a second apparatus, operably associated with the compressing apparatus, for electrically stimulating leg muscles as the driven blood from the foot passes therethrough. The resultant muscle activity enhances the blood flow velocity to the point where endothelial derived relaxing factor (EDRF) is produced, which dilates the blood vessel and enables a higher flowrate of blood to be delivered.

Significantly, U.S. Pat. No. 5,674,262 teaches that electrical stimulation, in and of itself, is not efficacious for stimulating blood flow, and does not bring about EDRF production.

U.S. patent application Ser. No. 10/451,334 to Nachum teaches treatment methods for promoting a localized increase in the flow of blood through a blood vessel in an area of the body. In these treatment methods, electrical impulses from the signal generator are applied to body tissue, by means of electrodes, so as to subject the adjacent muscular tissue to at least one voltage differential, thereby inducing a repeated, contracting movement of muscular tissue associated with the local blood vessels. This movement of muscular tissue produces a localized increase in the flow of blood through these blood vessels.

In preferred embodiments, treatment is effected by placing the electrodes at opposite ends of the limb segment, and applying the electrical impulses so as to establish a voltage differential between the electrodes. The voltage differential is made up of two wave forms propagated in opposite directions between the electrodes.

U.S. patent application Ser. No. 10/451,334 teaches that the timing between these wave forms is critical, and that there should be a time overlap between them of 1 to 500 microseconds, and more preferably, between 10 microseconds and 100 microseconds. It will be appreciated that in practice, the requisite synchronization is difficult to achieve, such that the method is of limited efficacy.

There is therefore a recognized need for, and it would be highly advantageous to have, an improved, efficacious device and method for more efficiently promoting, upon demand, the localized circulation of blood through blood vessels. It would be of further advantage if the device and method would be simple, robust, non-invasive, repeatable, and adjustable to the individual needs of the patient.

SUMMARY OF THE INVENTION

The present invention successfully addresses the shortcomings of the existing technologies by providing a device and method of enhancing, or reducing, a localized flow of blood, in a substantially painless, external, non-invasive manner. The device of the present invention is simple, easy to adjust, readily adaptable to the needs of a specific patient, and can be operated by the typical patient.

According to the teachings of the present invention there is provided a non-invasive method for promoting a localized change in a flow of blood through a blood vessel in a limb segment of a body by a series of electrically stimulated contractions of muscle tissue in the limb segment, the method including the steps of: (a) providing a device including: (i) a plurality of electrodes including at least a first electrode, a second electrode, and a third electrode, each of the electrodes for operatively contacting the limb segment of the body; (ii) a signal generator, operatively connected to each electrode, for producing a series of electrical impulses to the limb segment via the plurality of electrodes, the signal generator for connecting to a power supply, and (iii) a control unit, associated with the signal generator, for controlling the signal generator so as to produce the series of electrical stimulation impulses, the impulses being of pre-determined voltage differential, form, and duration; (b) positioning the plurality of electrodes on the limb segment; (c) applying at least one of the electrical impulses so as to induce a substantially radial contraction of a first portion of the muscular tissue in the limb segment; (d) applying at least one of the electrical impulses so as to induce a substantially longitudinal contraction of a second portion of the muscular tissue in the limb segment, such that the muscular tissue acts upon the blood vessel to produce the localized change in the flow of blood through the limb segment.

According to further features in the described preferred embodiments, the device further includes: (iv) a switching mechanism, responsive to the control unit, designed and configured for switching electrical connections between the signal generator and each of the electrodes, according to a pre-determined sequence.

According to further features in the described preferred embodiments, the substantially radial contraction is induced by providing at least a first voltage differential between the first electrode and the second electrode, and wherein the substantially longitudinal contraction is induced by providing at least a second voltage differential between the second electrode and the third electrode.

According to further features in the described preferred embodiments, the method further includes the step of: (e) switching electrical connections, by means of the switching mechanism, between the signal generator and each of the electrodes, so as to deliver the series of electrical stimulation impulses.

According to further features in the described preferred embodiments, the localized change is an increase in the flow of blood through the blood vessel.

According to further features in the described preferred embodiments, the localized change is a decrease in the flow of blood through the blood vessel.

According to further features in the described preferred embodiments, the series of electrical impulses includes a plurality of voltage differential peaks, each of the peaks having a duration of 80-1200 microseconds.

According to further features in the described preferred embodiments, the series of electrical impulses includes a plurality of voltage differential peaks, each of the peaks having a duration of 100-600 microseconds.

According to further features in the described preferred embodiments, the device further includes: (iv) a switching mechanism, responsive to the control unit, designed and configured for switching electrical connections between the signal generator and each of the electrodes, according to a pre-determined sequence, so as to deliver the series of electrical stimulation impulses by providing at least a first voltage differential between the first electrode and the second electrode, a second voltage differential between the second electrode and the third electrode, and a third voltage differential between the third electrode and another electrode of the plurality of electrodes.

According to further features in the described preferred embodiments, steps (c) and (d) are performed such that the longitudinal contraction is induced while the first portion of the muscular tissue remains at least partially contracted.

According to still further features in the described preferred embodiments, the radial contraction is effected upstream of the longitudinal contraction.

According to still further features in the described preferred embodiments, the method further includes the step of: (e) applying at least one of the electrical impulses so as to induce a second substantially radial contraction of a third portion of the muscular tissue in the limb segment.

According to still further features in the described preferred embodiments, the second radial contraction is effected downstream of the longitudinal contraction.

According to still further features in the described preferred embodiments, the "another electrode", referred to hereinabove, is a fourth electrode of the plurality of electrodes.

According to another aspect of the present invention there is provided a non-invasive device for promoting a localized increase or decrease in a flow of blood through a blood vessel in a limb segment of a body, the device including: (a) a plurality of electrodes including at least a first electrode, a second electrode, and a third electrode, each of the electrodes for operatively contacting the limb segment of the body; (b) a signal generator, operatively connected to each electrode, for providing a series of electrical impulses to the limb segment via the plurality of electrodes, the signal generator for connecting to a power supply; (c) a control unit, associated with the signal generator, for controlling the signal generator so as to produce the series of electrical stimulation impulses, the impulses being of pre-determined voltage differential, form, and duration, and (d) a switching mechanism designed and configured for switching electrical connections between the signal generator and each of the electrodes, according to a pre-determined sequence, so as to provide a first voltage differential between the first electrode and the second electrode, a second voltage differential between the second electrode and the third electrode, and a third voltage differential between the third electrode and another electrode of the plurality of electrodes.

According to further features in the described preferred embodiments, the control unit is designed and configured such that when the plurality of electrodes is disposed on the limb segment, the first, second and third voltage differentials promote a localized change in the flow of blood through the blood vessel.

According to still further features in the described preferred embodiments, the switching mechanism is responsive to the control unit.

According to still further features in the described preferred embodiments, the control unit and the switching mechanism are configured such that a frequency of the series of electrical stimulation impulses delivered to the electrodes is 1-30 periods per minute, and more preferably, 5-20 periods per minute.

According to still further features in the described preferred embodiments, the signal generator and the control unit are designed and configured such that the series of electrical impulses has a cycle frequency in the range of 0.5-20 Hz, and more preferably, in the range of 6-15 Hz.

According to still further features in the described preferred embodiments, the control unit is designed and configured such that when the plurality of electrodes is disposed on the limb segment, the first, second and third voltage differentials induce at least one substantially radial contraction of a first portion of the muscular tissue in the limb segment, at least partially followed by substantially longitudinal contraction of a second portion of the muscular tissue in the limb segment, so as to effect the localized change in the flow of blood through the blood vessel.

According to yet another aspect of the present invention there is provided a non-invasive device for promoting a localized change in a flow of blood through a blood vessel in a limb segment of a body, the device including: (a) a plurality of electrodes including at least a first electrode, a second electrode, and a third electrode, each of the electrodes for operatively contacting the limb segment of the body; (b) a signal generator, operatively connected to each electrode, for providing a series of electrical impulses to the limb segment via the plurality of electrodes, the signal generator for connecting to a power supply; (c) a control unit, associated with the signal generator, for controlling the signal generator so as to produce the series of electrical stimulation impulses, the impulses being of pre-determined voltage differential, form, and duration, wherein the control unit is designed and configured such that when the plurality of electrodes is disposed on the limb segment, the series of electrical stimulation impulses induces at least one substantially radial contraction of a first portion of the muscular tissue in the limb segment, the radial contraction at least partially followed by a substantially longitudinal contraction of a second portion of the muscular tissue in the limb segment, so as to effect the localized change in the flow of blood through the limb segment.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

The file of this patent contains at least one color photograph. Copies of this patent with color photograph(s) will be provided by the Patent and Trademark Office upon request and payment of necessary fee In the drawings.

DESCRIPTION OF THE PREFERRED EMBODIMENTS

Figure 1:
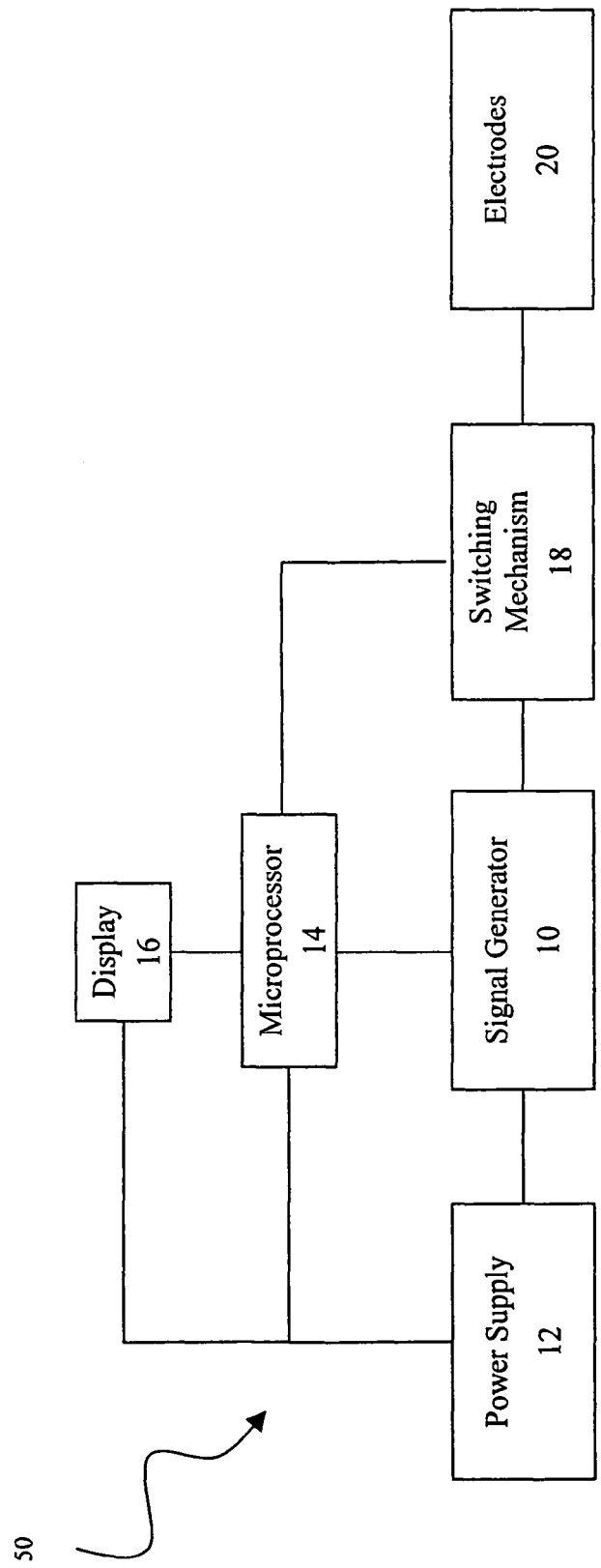
FIG. 1 is a block diagram that conceptually shows the main components of the device of the present invention.

According to the teachings of the present invention there is provided a method and device for externally promoting a localized increase in a flow of blood through a blood vessel in a particular area of the body.

Typically, this repeated contractual movement of voluntary muscular tissue can be harnessed to drive the oxygenated blood through the arteries to a limb extremity, and subsequently, to drive the oxygen-depleted blood back towards the heart, the net result being an increase in the supply of blood to the limb extremity.

Alternatively, the sequence of the repeated contractual movement of muscular tissue can be reversed, such that the flow of blood to a given area is reduced.

The principles and operation of this process according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

As used herein in the specification and in the claims section that follows, the term "voltage differential" refers to an absolute difference between two distinct voltage values.

As used herein in the specification and in the claims section that follows, the term "radial muscle contraction" and the like, with respect to a limb segment, refers to an instrumentally induced muscle contraction that is perpendicular or generally perpendicular to the general flowpath of blood through the limb segment, so as to momentarily reduce, or completely curtail, the flow of blood from a point upstream of the contraction to a point downstream of the contraction.

As used herein in the specification and in the claims section that follows, the term "longitudinal muscle contraction" and the like, with respect to a limb segment, refers to an instrumentally induced muscle contraction that is parallel or substantially parallel to the general flowpath of blood through the limb segment.

Referring now to the drawings, FIG. 1 is a block diagram showing the components of a stimulation device 50 according to the present invention. Signal generator 10 is operatively connected to a power supply 12. Also connected to power supply 12, are control unit or microprocessor 14 and display 16. Signal generator 10 can also be integral with microprocessor 14. Signal generator 10 is also operatively connected to a plurality of electrodes 20 via switching mechanism 18. Control unit 14 controls signal generator 10 so as to produce a series of electrical stimulation impulses. These impulses are delivered to electrodes 20 positioned on a limb segment of the patient, as will be explained in further detail hereinbelow. Switching mechanism 18 determines to which pair of electrodes the stimulation impulses will be delivered. Switching mechanism 18 can also be configured as a distributing mechanism that simultaneously distributes a positive or negative signal to two or more electrodes.

Thus, as used herein in the specification and in the claims section that follows, the term "switching mechanism" and the like, is meant to include a distributing mechanism that concurrently distributes a positive signal to two or more electrodes, or a negative signal to two or more electrodes.

Switching mechanism 18 can be a mechanical switching system, an electromechanical relay mechanism, or preferably, an electrical/electronic switching system controlled by control unit 14. A solid state relay having a photo-sensitive metal oxide semiconductor effect transistor (MOSFET) device with an LED to actuate the device is one presently preferred embodiment for switching mechanism 18.

Display 16, which is responsive to control unit 14, is advantageously configured to display information such as signal frequency, pulse width, period, and voltage.

Figure 2A:
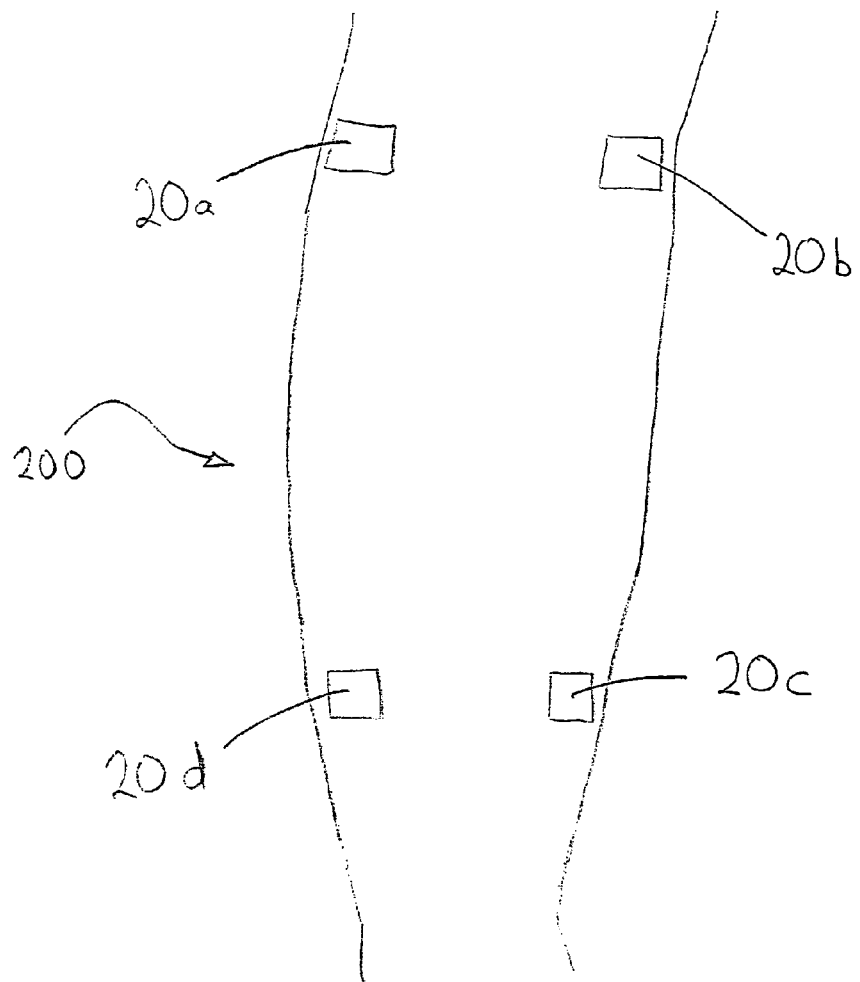
FIG. 2A provides a schematic illustration of a section of a lower leg, to which are affixed two electrode pairs, according to the present invention.
Figure 2B:
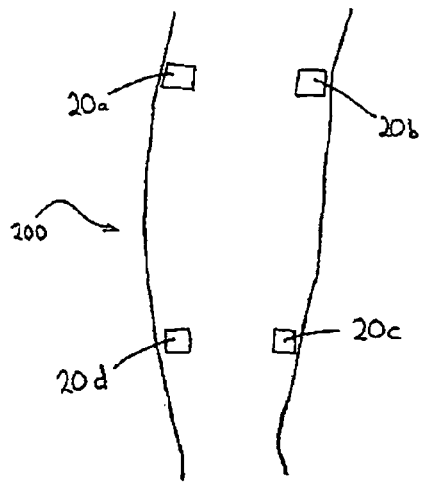
FIGS. 2B-2E is a schematic representation of the inventive contraction timing sequence provided by the control unit, by means of the switching mechanism, according to the present invention.
Figure 2C:
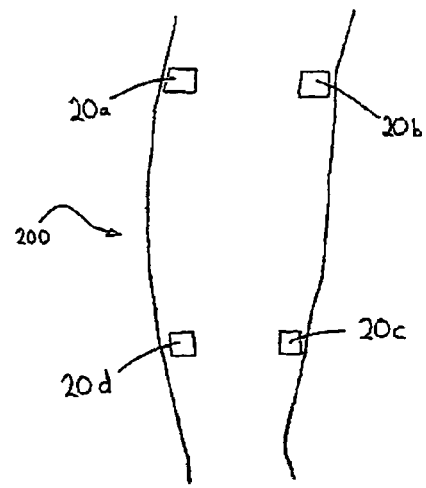

FIG. 2A provides a schematic illustration of a section of a limb segment such as lower leg 200, to which are affixed electrodes 20a-d, according to the present invention. A first pair of electrodes 20a-b is affixed at an upper end of lower leg 200 and a second pair of electrodes 20c-d is affixed at the opposite end of lower leg 200. Electrodes 20a-d are preferably positioned near the ends of the muscles of lower leg 200. Electrodes 20a-d are operatively connected to stimulation device 50 via switching mechanism 18, as shown in FIG. 1.

By applying a suitable voltage differential and current to electrodes 20a-d, muscular tissue in lower leg 200 contracts, thereby impinging upon the local blood vessels. It has been discovered by the inventor that with the proper electrical impulses and contraction positioning (constriction points), and timing sequence, the device of the present invention can be utilized to appreciably, measurably, and repeatably enhance the flow of blood through the limb segment.

The inventive contraction timing sequence will now be described, by way of example, with reference to FIGS. 1 and 2A, and in particular, with reference to FIG. 2B-2E. In step (I), shown schematically in FIG. 2B, switching mechanism 18 delivers a voltage differential from signal generator 10 (not shown) to first pair of electrodes 20a-b disposed at an upper end of lower leg 200. The resulting muscular contraction is substantially a radial muscular contraction 40 between electrodes 20a-b. In step (II), shown schematically in FIG. 2C, switching mechanism 18 delivers a voltage differential from signal generator 10 to an electrode from first pair of electrodes 20a-b and to an electrode from second pair of electrodes 20c-d disposed at a lower end of lower leg 200. By way of example, switching mechanism 18 delivers a positive voltage to electrode 20b and a negative voltage to electrode 20c. The resulting muscular contraction is substantially a longitudinal muscular contraction 42 along the length of lower leg 200.

Figure 2D:
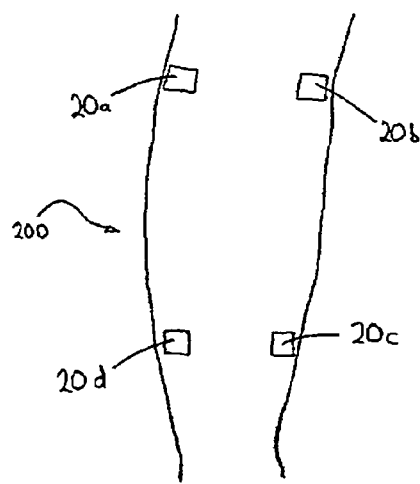

In step (III), shown schematically in FIG. 2D, switching mechanism 18 delivers a voltage differential from signal generator 10 to second pair of electrodes 20c-d. The resulting muscular contraction is substantially a radial muscular contraction 44 between electrodes 20c-d at or towards a lower end of lower leg 200. By way of example, switching mechanism 18 delivers a positive voltage to electrode 20c and a negative voltage to electrode 20d.

Figure 2E:
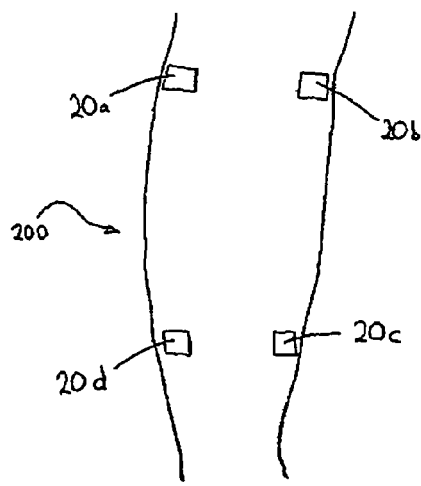

Step (IV), shown schematically in FIG. 2E, completes the cycle: switching mechanism 18 delivers a voltage differential from signal generator 10 to an electrode from first pair of electrodes 20a-b and to an electrode from second pair of electrodes 20c-d, so as to effect a substantially longitudinal muscular contraction 46 along the length of lower leg 200. By way of example, switching mechanism 18 delivers a positive voltage to electrode 20d and a negative voltage to electrode 20a.

It must be emphasized that the various known electrical stimulation devices for promoting a localized increase in the flow of blood are designed, configured, and operated so as to effect, solely, a substantially longitudinal muscular contraction along the length of the lower leg. However, effecting both radial muscular contractions and longitudinal muscular contractions so as to promote a localized increase in the flow of blood is not disclosed.

Without wishing to be limited by theory, the inventor attributes the enhanced flow of blood to a timed succession of electrically-induced muscular contractions, the succession including at least one radial contraction followed by at least one longitudinal contraction. Preferably, the electrical signals that precipitate the longitudinal contraction should be timed such that the radial contraction is still at least partially in effect, as shown by the dashed or solid lines 40a, 42a, and 44a in FIGS. 2C-2E. It is known that muscle tissue fundamentally differs from an ideal resistor in that a muscle is an extremely complex resistor having an inherent lag time, after providing the requisite electrical stimulation, until contraction occurs, and having an inherent lag time, after stopping the stimulation, until contraction completely subsides. The present invention utilizes the inherent relaxation lag time after stopping (or reducing) the stimulation to the limb segment. The radial contractions greatly reduce the fluid communication between the downstream vessels below the constriction point and the upstream vessels disposed above the constriction point (i.e., closer to the heart on the blood flowpath). This phenomenon contributes to the efficacy of the longitudinal contraction, in which much of the blood in the arteries in the limb segment is forced out of the limb segment. Since the return flowpath to the heart is temporarily closed or constricted, the blood in the limb segment is forcefully driven into the blood/oxygen-deficient extremities, which has become the path of least resistance.

Alternatively or additionally, switching mechanism 18 can also be configured as a distributing mechanism that simultaneously distributes a positive voltage to two or more electrodes, or a negative voltage to two or more electrodes, as shown in FIG. 2E, where radial contraction 44a is induced, at least partly, by the voltage differential that is delivered to electrodes 20c and 20d concurrently with the voltage differential that is delivered to electrodes 20d and 20a.

Referring again to FIGS. 2B-2E, a localized decrease in the flow of blood can be achieved by substantially reversing the sequence described hereinabove. Thus, by way of example, radial contraction 44 of FIG. 2D is induced, followed by longitudinal muscular contraction 42 of FIG. 2C.

Figure 3:
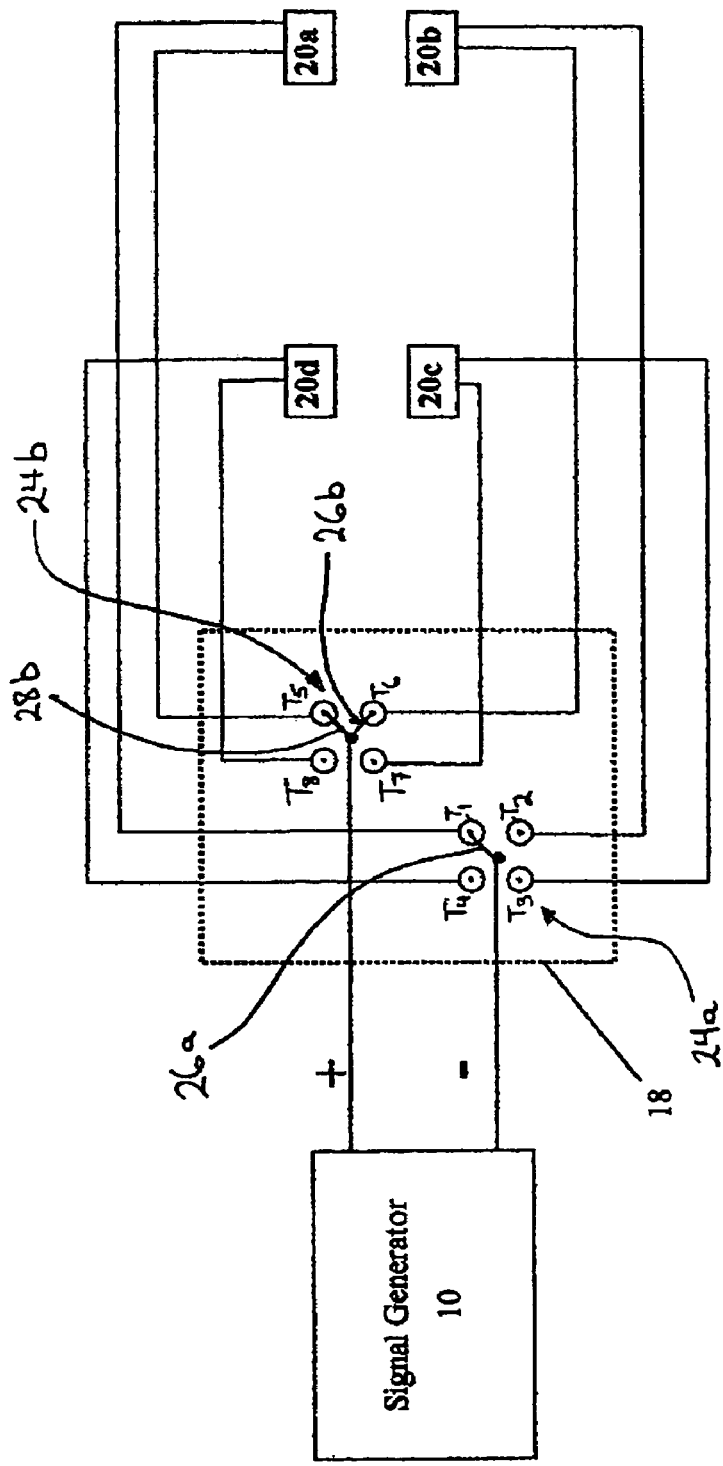
FIG. 3 is a diagram showing an exemplary switching arrangement for the switching mechanism of the inventive device, and the electrical connections between the switching mechanism, the signal generator, and the surface electrodes.

FIG. 3 is a diagram showing an exemplary switching arrangement for switching mechanism 18, and the electrical connections between switching mechanism 18, signal generator 10, and surface electrodes 20a-d. Signal generator 10 and switching mechanism 18 are electrically connected by a positive electrical connection and by a negative electrical connection. The negative electrical connection connects to a first switch 24a having terminals $T_1$-$T_4$, by means of rotating electrical connector 26a, and the positive electrical connection connects to a second switch 24b having terminals $T_5$-$T_8$, by means of rotating electrical connector 26b. As described hereinabove, switching mechanism 18 can have an additional electrical connector (e.g., electrical connector 28b) for concurrently providing two or more positive electrical connections, or two or more negative electrical connections, so as to distribute a positive voltage between two or more electrodes, or to distribute a negative voltage between two or more electrodes.

In the switch positions depicted in FIG. 3, signal generator 10 is negatively connected, via terminal $T_1$, to electrode 20a, and positively connected, via terminal $T_6$, to electrode 20b (assuming that optional connector 28b is not connected). In these switch positions, electrodes 20c and 20d are not electrically connected. Thus, with signal generator 10 connected to a power supply, and with stimulation device 50 disposed on a limb segment such as lower leg 200, as shown in FIG. 2A, a voltage differential between electrodes 20a and 20b would effect a radial contraction of the muscles.

Figure 4:
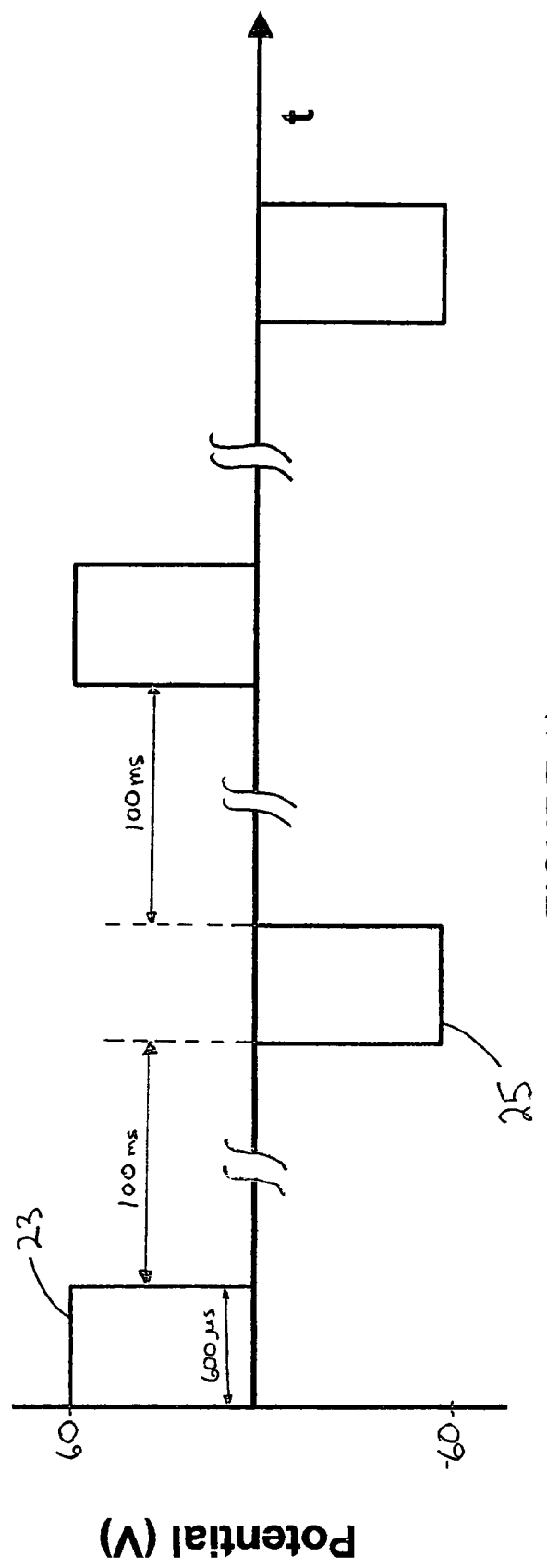
FIG. 4 is an exemplary voltage vs. time graph, according to the inventive treatment method and device of the present invention.
Figure 5A:
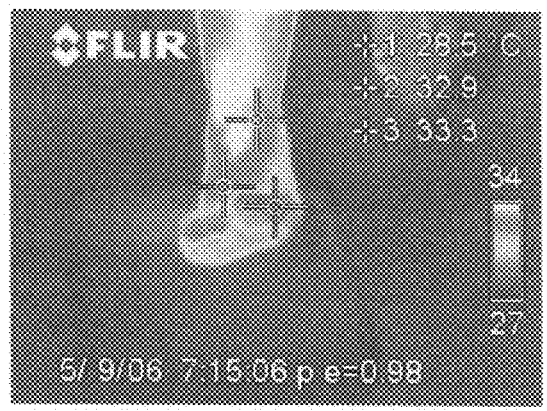
FIGS. 5A-5D are thermographs recorded intermittently during the course of a Transcutaneous Electrical Nerve Stimulation (TENS) treatment using a prior art TENS device.
Figure 5B:
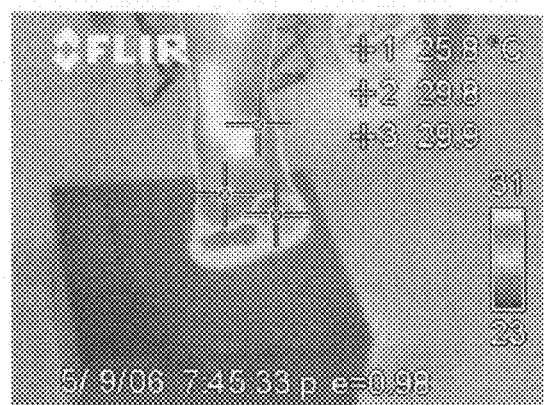
Figure 5C:
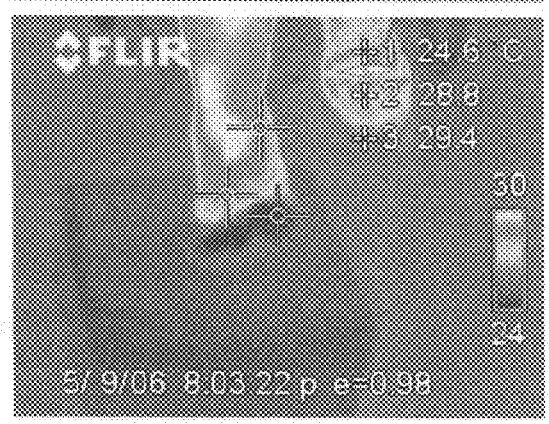
Figure 5D:
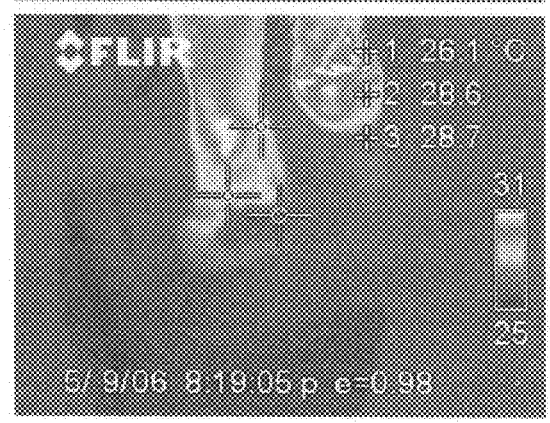

FIG. 4 shows an exemplary voltage vs. time graph for a treatment method according to the present invention, using the inventive device described hereinabove. The impulses provided are square waves having an intensity of 60 Volts. The duration of each square wave is approximately 600 microseconds. The time axis has not been drawn to scale, in order to fit 2 full cycles in the graph.

Typically, each step described with respect to FIGS. 2B-2E includes 3-30 of such impulses.

The time interval between positive impulses (or between negative impulses) is approximately 100 milliseconds. Thus, the cycle frequency (one positive and one negative impulse) is about 10 cycles per second, i.e., about 10 Hz. Although only 4 impulses are shown in FIG. 4, it will be appreciated that a practical treatment requires a large plurality of such impulses.

The initial impulse 23 provided to electrode pair 20a and 20b by signal generator 10 has a positive voltage differential (+60 Volts). The second impulse 25 applied to electrode pair 20b and 20c by signal generator 10 has a negative voltage differential of −60 Volts.

More generally, the voltage differential is up to 80V, and more typically, 30-60V, depending, inter alia, on the impedance of the patient's skin. The cycle frequency is 0.5-20 Hz, more preferably, 6-15 Hz.

Preferably, signal generator 10 is designed and configured to deliver the electrical signals at a rate of 1-30 periods per minute, and more preferably, 5-20 periods per minute.

As used herein in the specification and in the claims section that follows, the term "period", with regard to electrical signals delivered to the electrodes, refers to a repeating sequence, between at least three electrodes, of at least one radial contraction and at least one longitudinal contraction, effected at least partially in series. Thus, Step I, Step II, Step III, and Step IV, as described hereinabove, followed by Step I, Step II, Step III, and Step IV, represents two periods. A sequence of Step I, Step II, Step I, Step II, Step I, Step II, represents three periods. The term "repeating sequence" is meant to include semi-repetitive sequences. Thus, the sequence of Step I, Step II, Step III, and Step IV, followed by Step I, Step II (without Step III and Step IV), followed by Step I, Step II, Step III, and Step IV, represents three periods.

As used herein in the specification and in the claims section that follows, the term "upstream", with regard to a first position in the blood flowpath of a body, refers to a position that is closer to the heart, along the blood flowpath. Similarly, the term "downstream", with regard to a first position in the blood flowpath of a body, refers to a position that is farther from the heart, along the blood flowpath.

As used herein in the specification and in the claims section that follows, the term "another electrode", with respect to a plurality of at least a first, second and third electrode for operatively contacting a limb segment of a body, refers either to the first electrode, or an additional electrode (such as a fourth electrode) other than the second and third electrodes.

It must be emphasized that various frequencies and wave forms have been found to be effective in conjunction with the method of the present invention. Appropriate wave forms include square waves, waves of transcendental functions, spikes, linear functions, and stepped patterns. Frequencies vary greatly, depending on the general health of the client, the type and duration of the treatment, etc. Hence, it is preferable that the device be configured such that an experienced operator can adjust, with facility, various parameters, including wave form, frequency, and intensity, by means of microprocessor 14.

The frequency, the number, the intensity and the duration of muscle contractions are controlled by the nature of the signals passed to the electrodes. The localized increase in the flow of blood effected by the device and method of the present invention is important for a wide variety of medical applications, including but not limited to rehabilitating muscular response affected by trauma or inactivity, decreasing the amount of water retained, as in case of the lower limbs, improving blood and lymph circulation, thereby alleviating pain, therapy related to controlling the function of erectile tissue, and speeding up healing, particularly in the case of diabetic patients. The restriction of blood flow by inducing the repeated contractual movement of muscular tissue against the natural flow of blood is also germane to a wide variety of medical applications, including various surgical procedures and edema reduction.

EXAMPLES

Reference is now made to the following examples, which together with the above descriptions, illustrate the invention in a non-limiting fashion.

Example 1

Figure 6:
FIG. 6 is a plot of the temperature profile of three monitoring points on the foot, as a function of time, based, inter alia, on the thermographs of FIGS. 5A-5D.

A conventional Transcutaneous Electrical Nerve Stimulation (TENS) device was used to provide electrical stimulation to the lower leg of a patient suffering from poor circulation in the foot. A first surface electrode of the device was positioned underneath the knee, and a second electrode of the device was positioned above the calf. Electrical stimulation was administered for over 60 minutes. A FLIR™ ThermaCAM® EX320 was used to thermally monitor the foot and lower calf. In particular, three locations on the leg were monitored:
 (1) a point on the big toe;
 (2) a point on the instep;
 (3) a point on the lower calf.
Thermographs recorded intermittently during the course of the stimulation treatment are provided in FIGS. 5A-5D. Initially, the lower leg and calf regions, including lower calf point 3, are at a temperature of 33-34 C; the instep, including instep point 2, is at a temperature of 33-34 C; big toe point 1 is at 28.5 C. After about 30 minutes, the temperatures in the toe, instep, and lower calf have not improved; if anything, a decrease of 2-3 C is indicated. Subsequently, the temperatures at the three monitoring points remain fairly constant, such that after an hour, the temperature at big toe point 1 is still 2 C below the initial temperature. The temperature profile of the three monitoring points is provided in FIG. 6.

It is thus evident that this conventional (TENS) device and treatment method did not measurably increase the localized blood flow in the extremities of the stimulated leg.

Example 2

A device of the present invention was used to provide electrical stimulation to the lower leg of a patient suffering from poor circulation in the foot. Two surface electrodes of the inventive device were positioned underneath the knee, and an additional two surface electrodes of the device were positioned above the calf, substantially as shown in FIG. 2A. The microprocessor used for controlling the device was an ATMEL® 8 bit AVR® microcontroller, model no. ATmega8535, which also contains the signal generator unit.

Electrical stimulation was administered for over 60 minutes. As in Example 1, a FLIR™ ThermaCAM® EX320 was used to thermally monitor the foot and lower calf. In particular, three locations on the leg were monitored:

(1) a point on the big toe;
(2) a point at the base of the big toe;
(3) a point on the instep.

Thermographs recorded intermittently during the course of the stimulation treatment are provided in FIGS. 7A-7F. In the first thermograph provided in FIG. 7A, taken about 4 minutes after stimulation was initiated, the lower leg and calf regions (not shown) are at a temperature of at least 32 C, instep point 3 is at a temperature of 27.5 C; big toe base point 2 is at 23.5 C, and big toe point 1 is at about 20 C. In this thermograph image, all five toes are blue to deep blue, indicating a temperature of ~17-18 C. The second thermograph (FIG. 7B), taken about 20 minutes later, is substantially identical to the first thermograph. A slight warming of the smaller toes is observed.

Figure 7A:
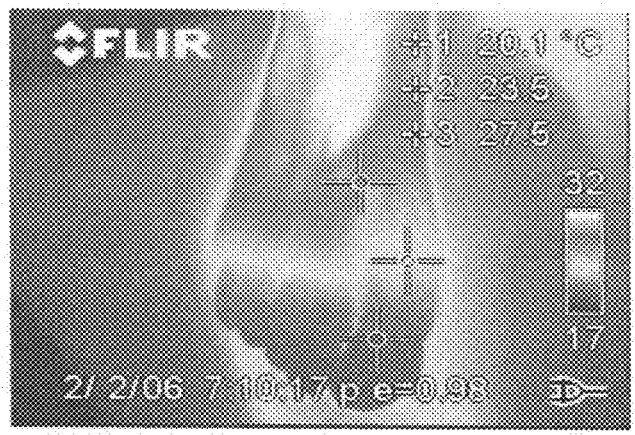
FIGS. 7A-7F are thermographs recorded intermittently during the course of an electrical stimulation treatment using the device of the present invention.
Figure 7B:
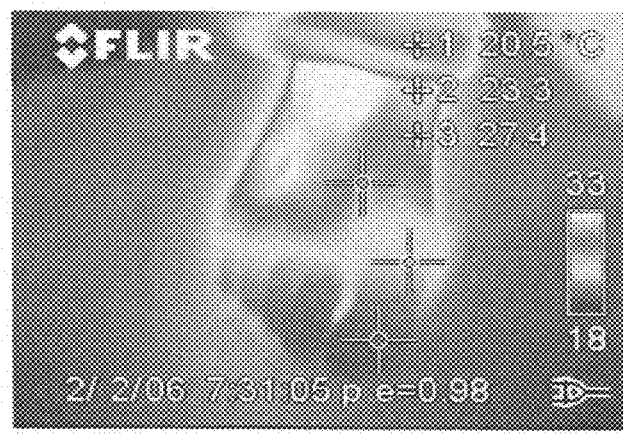
Figure 7C:
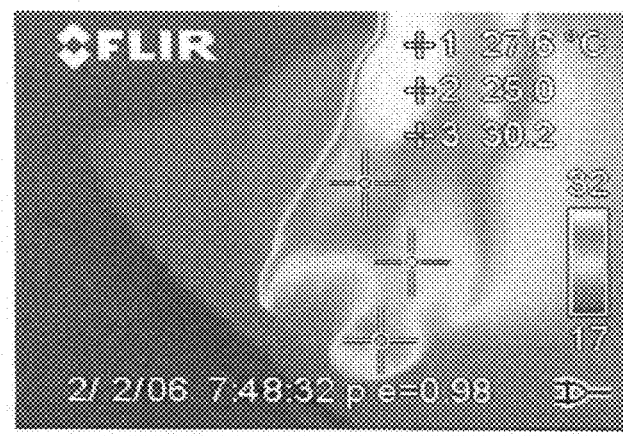

In the third thermograph provided in FIG. 7C, taken about 43 minutes after stimulation was initiated, instep point 3 has undergone a temperature rise of about 3 C to 30.2 C; the temperature of big toe base point 2 has risen to 25 C, and big toe point 1 shows an appreciable temperature rise of about 7 C to 27.6 C. It is also evident from this thermograph image that all five toes have undergone warming.

Figure 7D:
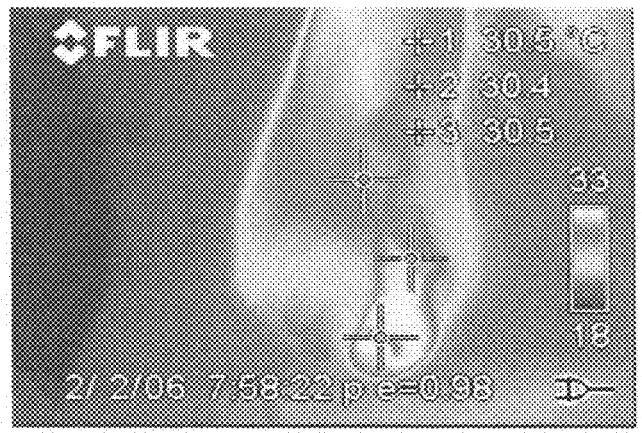
Figure 7E:
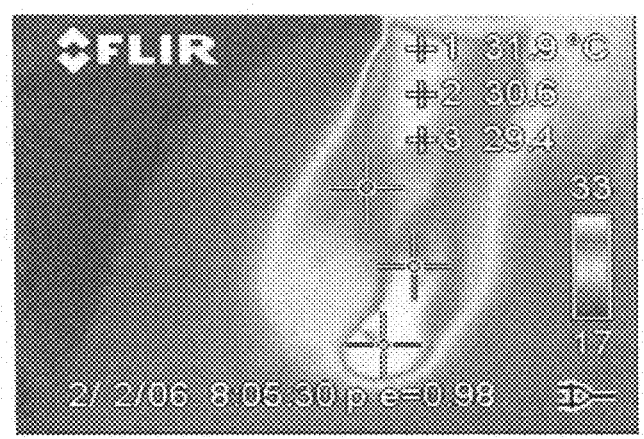

The fourth thermograph, provided in FIG. 7D, was taken about 53 minutes after stimulation was initiated. Instep point 3 is now at a temperature of 30.5 C; the temperature of big toe base point 2 has rapidly risen to 30.4 C, and big toe point 1 shows a temperature rise of another 3 C to 30.5 C. The other four toes also show signs of additional warming.

In the fifth thermograph (FIG. 7E), taken about one hour after stimulation was initiated, the measured points are similar to those of FIG. 7D. The four smaller toes continue to the warming trend.

Figure 7F:
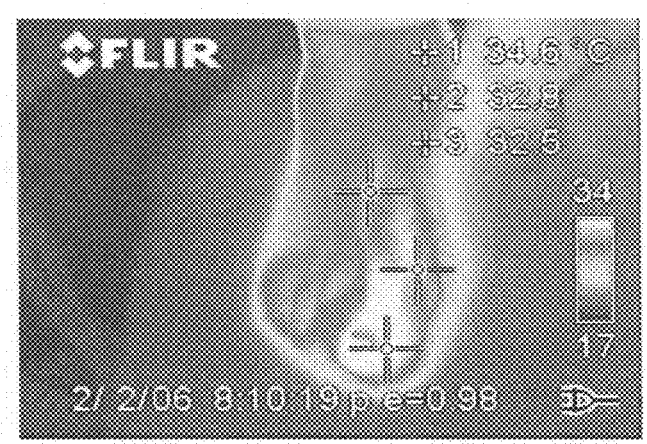

The final thermograph, provided in FIG. 7F, was taken about 65 minutes after stimulation was initiated. Instep point 3 is now at a temperature of 32.5 C; the temperature of big toe base point 2 has risen to 32.8 C, and big toe point 1 shows a temperature rise to 34.6 C. The other four toes continue to warm up, such that the entire foot appears to be within the range of 30 C-35 C.

Figure 8:
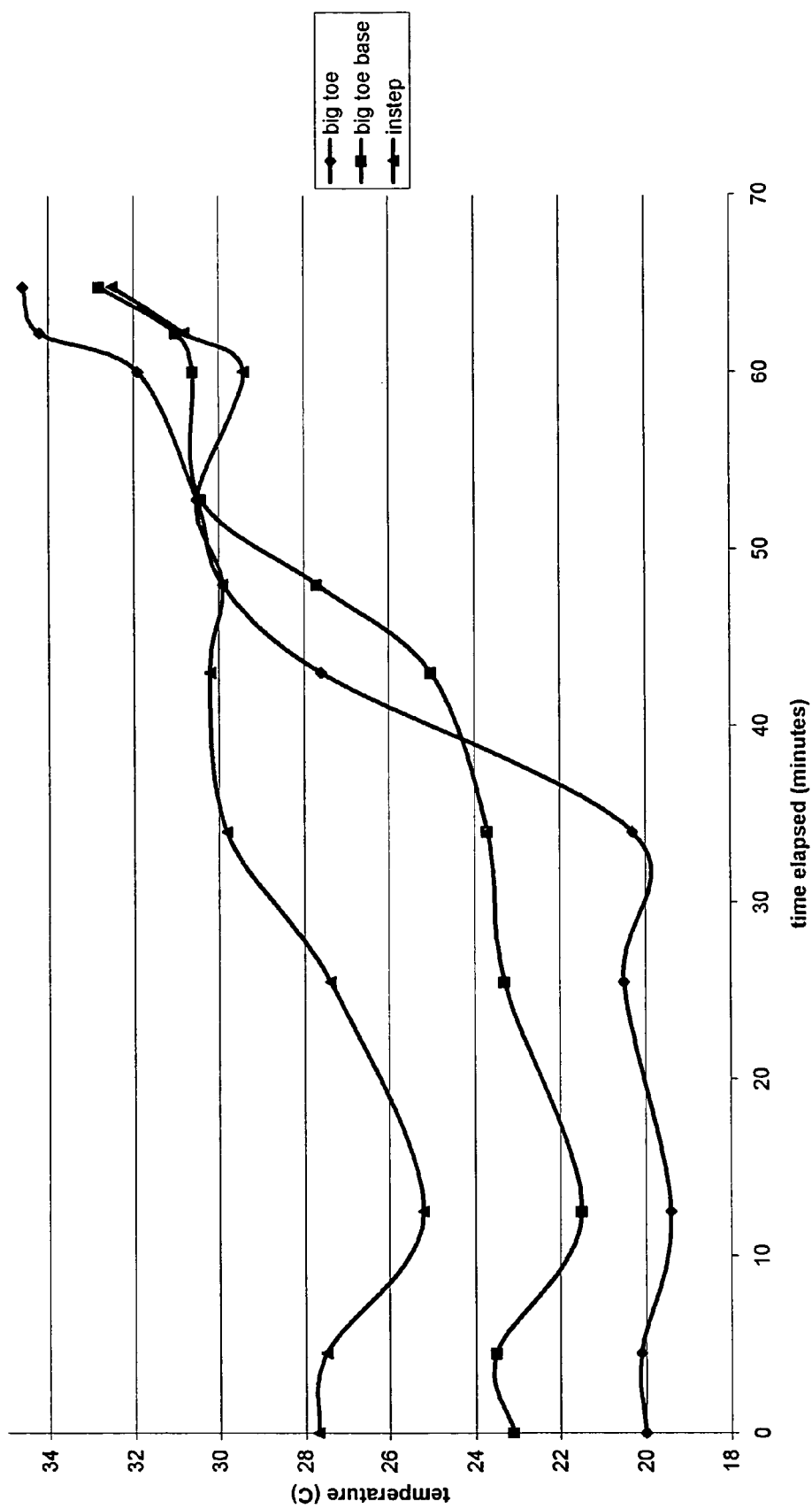
FIG. 8 is a plot of the temperature profile of three monitoring points on the foot, as a function of time, based, inter alia, on the thermographs of FIGS. 7A-7F.

The temperature profile of the three monitoring points, as a function of time, is provided in FIG. 8.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A non-invasive method for promoting a localized change in a flow of blood through a blood vessel in a limb segment on a lower leg of a body by a series of electrically stimulated contractions of muscle tissue in the limb segment, the method comprising the steps of:
    (a) providing a device including:
        (i) at least a first electrode, a second electrode, and a third electrode, each of said electrodes adapted to operatively contact the limb segment;
        (ii) a signal generator, operatively connected to each said electrode, adapted to produce a series of electrical impulses to the limb segment via said plurality of electrodes, said signal generator connecting to a power supply, and
        (iii) a control unit, associated with said signal generator, adapted to control said signal generator to produce said series of electrical impulses, said impulses being of pre-determined voltage differential, form, and duration;
    (b) positioning said plurality of electrodes on the limb segment, wherein said first electrode is positioned on a lower end of the lower leg, said second electrode is positioned on the lower leg, and said third electrode is positioned on an upper end of the lower leg, whereby said first electrode and said third electrode are disposed on opposite ends of the lower leg, and said second electrode and one of said first and third electrodes are disposed on a same end of the lower leg;
    (c) applying at least a first electrical impulse of said electrical impulses between said electrodes on said same end of the lower leg to induce a first muscular contraction of a first portion of the tissue in the lower leg;
    (d) applying at least a second electrical impulse of said electrical impulses between said first and third electrodes to induce a longitudinal muscular contraction of a second portion of the muscular tissue in the lower leg, whereby the muscular tissue acts upon the blood vessel to produce the localized change in the flow of blood through the lower leg, and wherein steps (c) and (d) are performed whereby said longitudinal contraction is induced while said first portion of the muscular tissue remains at least partially contracted by said first muscular contraction, and
    (e) delivering said electrical signals to said at least first, second, and third electrodes, whereby a repeating sequence of muscular contractions is effected, said repeating sequence including said muscular contraction of said first portion of the tissue and said longitudinal contraction.

2. The method of claim 1, wherein said frequency of said repeating sequence is 1-30 periods per minute.

3. The method of claim 2, wherein said frequency of said repeating sequence is 5-20 periods per minute.

4. The method of claim 1, wherein said plurality of electrodes includes a fourth electrode.

5. The method of claim 4, wherein said fourth electrode is positioned on an upper end of the lower leg.

6. The method of claim 5, wherein said repeating sequence of muscular contractions includes a muscular contraction of a third portion of the tissue in the lower leg, said contraction of said third portion of the tissue effected by applying at least one of said electrical impulses between said third electrode and said fourth electrode, on said upper end of the lower leg.

7. The method of claim 6, wherein said muscular contraction of said third portion of the tissue in the lower leg is effected downstream of said longitudinal contraction.

8. The method of claim 6, wherein said repeating sequence of muscular contractions, including said muscular contraction of said first portion of the tissue, said longitudinal contraction, and said muscular contraction of said third portion of the tissue, has a frequency of 1-30 periods per minute.

9. The method of claim 5, wherein said repeating sequence of muscular contractions includes a second longitudinal contraction of a third portion of the tissue in the lower leg, said second longitudinal contraction of said third portion of the tissue effected by applying at least one of said electrical impulses between said fourth electrode and at least one electrode disposed on said lower end of the lower leg.

10. The method of claim 9, wherein said repeating sequence of muscular contractions, including said muscular contraction of said first portion of the tissue, said longitudinal contraction, and said second longitudinal contraction, has a frequency of 1-30 periods per minute.

11. The method of claim 6, wherein said repeating sequence of muscular contractions includes a second longitudinal contraction of a fourth portion of the tissue in the lower leg, said second longitudinal contraction of said fourth portion of the tissue effected by applying at least one of said electrical impulses between said fourth electrode and at least one electrode disposed on said lower end of the lower leg.

12. The method of claim 11, wherein said repeating sequence of muscular contractions, including said muscular contraction of said first portion of the tissue, said longitudinal contraction, said muscular contraction of said third portion of the tissue, and said second longitudinal contraction, has a frequency of 1-30 periods per minute.

13. The method of claim 1, wherein the localized change is an increase in the flow of blood through the blood vessel.

14. The method of claim 13, wherein said duration of each of said electrical impulses is in a range of 80-120 microseconds.

15. The method of claim 13, wherein said duration of each of said electrical impulses is in a range of 100-600 microseconds.

16. The method of claim 1, wherein the localized change is a decrease in the flow of blood through the blood vessel.

17. The method of claim 1, wherein said muscular contraction of said first portion of the tissue is effected upstream of said longitudinal contraction.

18. The method of claim 1, wherein said muscular contraction of said first portion of the tissue is effected downstream of said longitudinal contraction.

19. The method of claim 1, wherein said electrical impulses of said series of electrical impulses are time-distinct impulses.

20. The method of claim 1, wherein at least said first electrical impulse is applied in a radial direction with respect to the lower leg.

21. A non-invasive method for promoting a localized change in a flow of blood through a blood vessel in a limb segment on a lower leg of a body by a series of electrically stimulated contractions of muscle tissue in the limb segment, the method comprising the steps of:
(a) providing a device including
  (i) at least a first electrode, a second electrode, and a third electrode, each of said electrodes adapted to operatively contact the limb segment of the body;
  (ii) a signal generator, operatively connected to each said electrode, adapted to produce a series of electrical impulses to the limb segment via said plurality of electrodes, said signal generator connecting to a power supply, and
  (iii) a control unit, associated with said signal generator, adapted to control said signal generator to produce said series of electrical impulses, said impulses being of pre-determined voltage differential, form, and duration;
(b) positioning said plurality of electrodes on the limb segment, wherein said first electrode is positioned on a lower end of the lower leg, above an ankle of said leg, said second electrode is positioned on the lower leg, and said third electrode is positioned on an upper end of the lower leg, whereby said first electrode and said third electrode are disposed on opposite ends of the lower leg, and said second electrode and one of said first and third electrodes are disposed on a same end of the lower leg;
(c) applying at least a first electrical impulse of said electrical impulses between said electrodes on said same end of the lower leg, in a radial direction with respect to a length of the lower leg, to induce a first muscular contraction of a first portion of the tissue in the lower leg;
(d) applying at least a second electrical impulse of said electrical impulses between said first and third electrodes to induce a longitudinal muscular contraction of a second portion of the muscular tissue in the lower leg, whereby the muscular tissue acts upon the blood vessel to produce the localized change in the flow of blood through the lower leg,
and wherein steps (c) and (d) are performed whereby said longitudinal contraction is induced while said first portion of the muscular tissue remains at least partially contracted by said first muscular contraction, and
(e) delivering said electrical signals to said at least first, second, and third electrodes, whereby a repeating sequence of muscular contractions is effected, said repeating sequence including said muscular contraction of said first portion of the tissue and said longitudinal contraction.

22. The method of claim 21, wherein said plurality of electrodes includes a fourth electrode, positioned on an upper end of the lower leg, wherein said repeating sequence of muscular contractions includes a muscular contraction of a third portion of the tissue in the lower leg, said contraction of said third portion of the tissue effected by applying at least one of said electrical impulses in a radial fashion with respect to said length of the lower leg, between said third electrode and said fourth electrode, on said upper end of the lower leg.

23. The method of claim 22, wherein said repeating sequence of muscular contractions includes a second longitudinal contraction of a fourth portion of the tissue in the lower leg, said second longitudinal contraction effected by applying at least one of said electrical impulses between said fourth electrode and said second electrode disposed on said lower end of the lower leg.

24. A non-invasive method for promoting a localized change in a flow of blood through a blood vessel in a limb segment on a lower leg of a body by a series of electrically stimulated contractions of muscle tissue in the limb segment, the method comprising the steps of:
(a) providing a device including:
  (i) at least a first electrode, a second electrode, and a third electrode, each of said electrodes adapted to operatively contact the limb segment of the body;
  (ii) a signal generator, operatively connected to each said electrode, adapted to produce a series of electrical impulses to the limb segment via said plurality of electrodes, said signal generator connecting to a power supply, and
  (iii) a control unit, associated with said signal generator, adapted to control said signal generator to produce said series of electrical impulses, said impulses being of pre-determined voltage differential, form, and duration;
(b) positioning said plurality of electrodes on the limb segment, wherein said first electrode is positioned on a lower end of the lower leg, said second electrode is positioned on the lower leg, and said third electrode is positioned on an upper end of the lower leg, whereby said first electrode and said third electrode are disposed on opposite ends of the lower leg, and said second electrode and one of said first and third electrodes are disposed on a same end of the lower leg;
(c) applying at least a first electrical impulse of said electrical impulses between said electrodes on said same end of the lower leg to induce a first muscular contraction of a first portion of the tissue in the lower leg;

(d) applying at least a second electrical impulse of said electrical impulses between said first and third electrodes to induce a longitudinal muscular contraction of a second portion of the muscular tissue in the lower leg, whereby the muscular tissue acts upon a blood vessel to produce the localized change in the flow of blood through the lower leg, and wherein steps (c) and (d) are perform whereby said longitudinal contraction is induced while said first portion of the muscular tissue remains at least partially contracted by said first muscular contraction, and (e) delivering said electrical signals to said at least first, second, and third electrodes, whereby a repeating sequence of muscular contractions is effected, said repeating sequence including said muscular contraction of said first portion of the tissue and said longitudinal contraction, wherein said frequency of said repeating sequence is 1-30 periods per minute.

25. The method of claim 24, wherein the lower leg has a particular length, and wherein said electrodes are positioned at opposite ends of the lower leg, whereby said longitudinal contraction is effected over substantially said particular length of the lower leg.

* * * * *